United States Patent
Waidman et al.

(10) Patent No.: US 10,437,169 B2
(45) Date of Patent: Oct. 8, 2019

(54) PHOTOCONDUCTOR CHARGING UNIFORMITY CORRECTION

(71) Applicant: HP INDIGO B.V., Amstelveen (NL)

(72) Inventors: Ran Waidman, Rehovot (IL); Sasi Moalem, Ness Ziona (IL); Kobi Shkuri, Ness Ziona (IL)

(73) Assignee: HP Indigo B.V., Amstelveen (NL)

( * ) Notice: Subject to any disclaimer, the term of this patent is extended or adjusted under 35 U.S.C. 154(b) by 0 days.

(21) Appl. No.: 16/065,936

(22) PCT Filed: Mar. 31, 2016

(86) PCT No.: PCT/EP2016/057163
§ 371 (c)(1),
(2) Date: Jun. 25, 2018

(87) PCT Pub. No.: WO2017/167388
PCT Pub. Date: Oct. 5, 2017

(65) Prior Publication Data
US 2019/0011848 A1    Jan. 10, 2019

(51) Int. Cl.
*G03G 15/02* (2006.01)
*G03G 15/00* (2006.01)
*G01N 27/61* (2006.01)

(52) U.S. Cl.
CPC ......... *G03G 15/0266* (2013.01); *G01N 27/61* (2013.01); *G03G 15/5037* (2013.01)

(58) Field of Classification Search
CPC ................ G03G 15/0266; G03G 15/5037
USPC .......................................... 399/38, 46, 48, 50
See application file for complete search history.

(56) References Cited

U.S. PATENT DOCUMENTS

| | | | |
|---|---|---|---|
| 6,166,550 A | 12/2000 | Abramsohn et al. | |
| 7,123,868 B2 | 10/2006 | Schultheis et al. | |
| 7,298,993 B2 * | 11/2007 | Lee .................... | G03G 15/0233 399/168 |
| 8,497,057 B2 | 7/2013 | Tombs et al. | |

(Continued)

FOREIGN PATENT DOCUMENTS

WO    WO-2012010202 A1    1/2012

OTHER PUBLICATIONS

Farahat A., Electrophotographic Printing Technology: Printing Process Steps and Dot Microstructure, Dec. 3, 2014.

(Continued)

*Primary Examiner* — Hoan H Tran
(74) *Attorney, Agent, or Firm* — HP Inc. Patent Department

(57) ABSTRACT

Examples of charging a photoconductive layer in an image forming apparatus are described. In one example, a method includes applying a charging voltage to the photoconductive layer and measuring surface voltages of the photoconductive layer at a plurality of positions on the photoconductive layer. Based on the measured surface voltages, a correction voltage profile is determined. The determined correction voltage profile includes at least a first correction voltage associated with a first position on the photoconductive layer and a second correction voltage associated with a second position, different to the first position, on the photoconductive layer. The method includes applying the first correction voltage to the photoconductive layer and applying the second correction voltage to the photoconductive layer.

18 Claims, 3 Drawing Sheets

(56) References Cited

U.S. PATENT DOCUMENTS

| | | |
|---|---|---|
| 8,849,136 B2 | 9/2014 | Reihl |
| 2002/0027591 A1 | 3/2002 | Itoh |
| 2005/0220468 A1* | 10/2005 | Kitajima ............ G03G 15/0266 |
| | | 399/48 |
| 2010/0040388 A1 | 2/2010 | Wagner |
| 2013/0077997 A1 | 3/2013 | Hanson et al. |

OTHER PUBLICATIONS

Wang J. et al., The Charging Process of Rollers in Print Engines with Atmospheric Pressure Plasmas, Aug. 8, 2013.

\* cited by examiner

PHOTOCONDUCTOR CHARGING UNIFORMITY CORRECTION

BACKGROUND

Electrophotography is commonly used in digital printers or presses. Digital printing may use a variety of print material to reproduce a variety of digital sources on a variety of media. Digital printers or presses may utilize a photoconductor to apply print material to a print medium. The photoconductor may be charged and exposed to light. Images produced by such systems comprise a series of dots. It is desirable to increase the uniformity of the sizes of these dots.

BRIEF DESCRIPTION OF THE DRAWINGS

Various features of the present disclosure will be apparent from the detailed description which follows, taken in conjunction with the accompanying drawings, which together illustrate, features of certain examples, and wherein.

DETAILED DESCRIPTION

In the following description and figures, some example implementations of an image forming apparatus, systems, and/or methods are described. An image forming apparatus using electrophotography may generate a constant or intermittent charge on a photoconductive layer during a print routine, or print cycle. Photoconductor charge affects the electrical field within the photoconductor, and thus affects the mobility of electric charges within the photoconductor. A light source selectively discharges the photoconductor to create an electrostatic image. The dot size created by the light source depends on the mobility of electric charges within the photoconductor. A lack of uniformity of the charge on the photoconductive layer causes an undesired lack of uniformity of the size of dots printed by the image forming apparatus. For example, in some printers, a 12 Volt difference in photoconductor charge alters the dot size by 1 micron (relative to a set point of 38 microns). Causes of non-uniformity of photoconductive layer charge include drum runout, and ageing of components.

Various examples described below were developed to counteract the effects of non-uniform photoconductor charging by applying a correction voltage profile to the photoconductive layer.

Figure 1A:
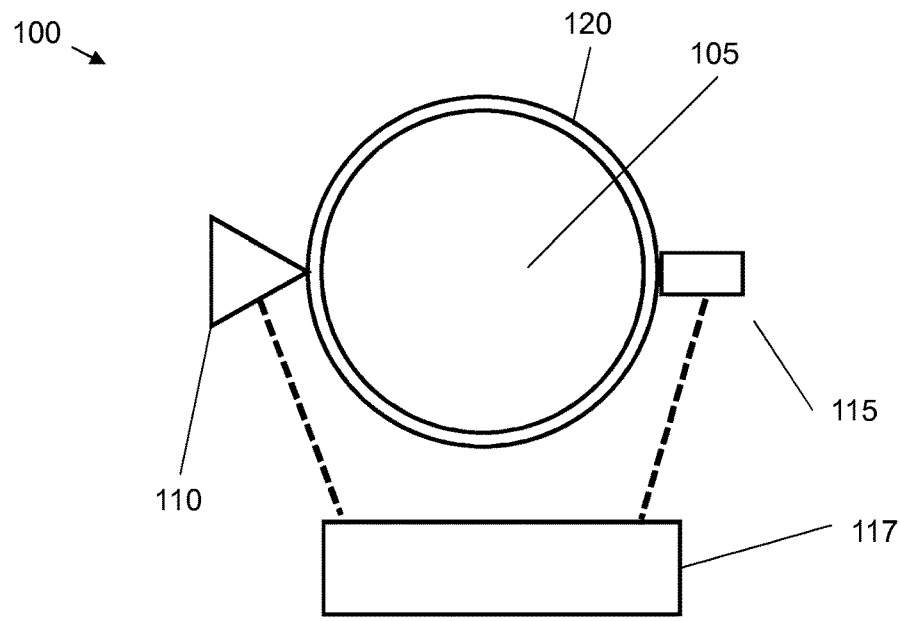
FIGS. 1A and 1B are schematic representations of image forming apparatus according to examples.

FIG. 1A is a schematic representation of an image forming apparatus 100 according to examples. In these examples, the image forming apparatus 100 includes a photoconductive unit 105 comprising a photoconductive layer 120, a charging unit 110, a measuring unit 115 and a controller 117. In an example, the charging unit comprises a charge roller. The photoconductive unit 105 may be a photoconductive drum, although in other examples may have a different form, such as a belt, or other transfer member. The photoconductive layer 120 may be an organic photoconductor, for example with a bi-layer structure comprising a charge generation layer and a charge transfer layer.

In certain examples, the photoconductive layer 120 can apply a print material to a print article (not shown). In certain examples, the print material is directly applied to the print article or indirectly applied by using for example an offset unit (not shown) for transferring the print material. In certain examples, an offset unit comprises an intermediate transfer member capable of transferring the print material from the photoconductive unit 105 to the print article.

In an example, the charging unit 110 is controllable by the controller 117 to apply a charging voltage to the photoconductive layer 120. The charging voltage may comprise a print voltage. In examples, the voltage is supplied by direct current, alternating current, pulsating current, variable current, or a combination of currents. "Voltage" may be discussed as a "charge voltage" or in conjunction with another modifier to denote the source of the voltage, but may otherwise have the same or similar characteristics of other voltages described herein.

As noted above, the uniformity of charging of the photoconductive layer 120 can be affected by various parameters, including drum runout, age of the charging unit 110, age of the photoconductive layer 120, and age of a blanket or intermediate transfer unit of the image forming apparatus. In certain examples, an intermediate unit comprises any chargeable component of an image forming apparatus capable of transferring a charge to the photoconductive layer 120 to electrically bias the photoconductive layer 120. In examples, an intermediate unit comprises at least one of a development unit, a transfer unit or intermediate transfer drum, an offset unit, a sponge unit, and a conductive layer of the photoconductive unit 105. The measuring unit 115 is controllable by the controller 117 to measure surface voltages of the photoconductive layer 120 at a plurality of positions on the photoconductive layer 120. In some examples, the measuring unit 115 comprises an electrostatic probe such as an electrostatic voltmeter. The measuring unit 115 may, alternatively or additionally, comprise an encoder.

In such an example, the controller 117 is configured to determine a correction voltage profile based on the measured surface voltages. The correction voltage profile comprises at least a first correction voltage associated with a first position on the photoconductive layer, and a second correction voltage associated with a second position, different to the first position, on the photoconductive layer. In examples, the correction voltage function comprises a continuous function of position. In other examples, the correction voltage profile comprises correction voltages associated with discrete positions. The controller 117 is further configured to initiate application of the first correction voltage to the first position on the photoconductive layer 120, and to apply the second correction voltage to the second position on the photoconductive layer 120. It is thus possible to correct the surface charge on the photoconductive layer 120, and thus the dot size, in a single charging cycle without requiring printing of a dot size test page. In some examples, the process is faster than printing a test page, and requires no waste of ink or substrate. The process reduces the required frequency and magnitude of performing a full uniformity correction.

Figure 1B:
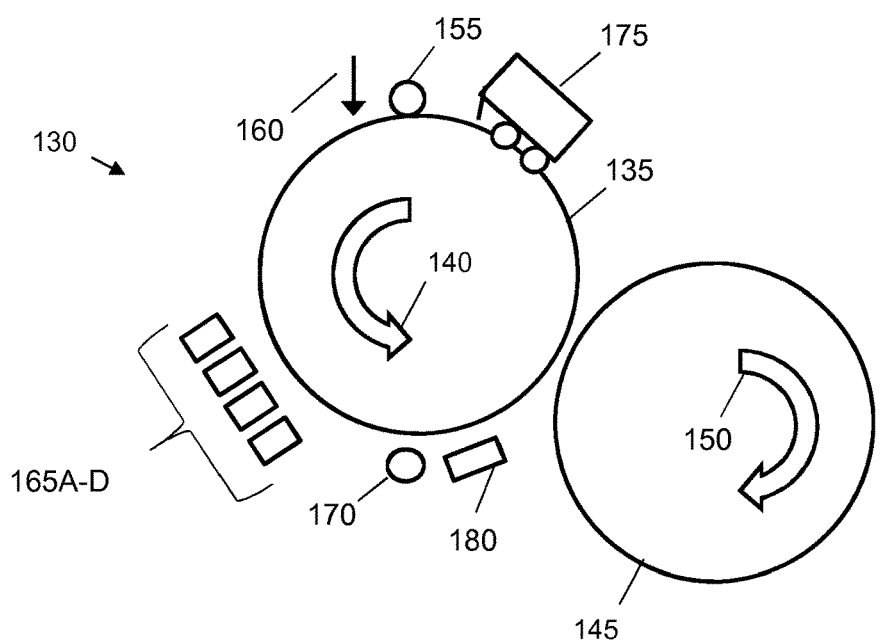

FIG. 1B is a more detailed schematic diagram showing a liquid electrophotographic printer 130 in accordance with an example.

Printer 130 comprises a photo imaging plate 135, which, in use, rotates in the direction indicated by arrow 140 and a heated blanket 145, which, in use, rotates in the direction indicated by arrow 150. The printer 130 further comprises a charging unit 110 and a laser 160. The printer 130 further comprises a plurality of image development units 165A-D, as well as a roller 170. In some examples, the printer also comprises a cleaning station 175 and a pre-transfer erase unit 180. In some examples, more than one of any of the above elements may be present.

In some examples, the pre-transfer erase unit 180 comprises a set of diodes to illuminate the photo imaging plate 135. Illumination causes a homogeneous conductivity across the photo imaging plate 135 leading to dissipation of the charges still existing on the background. This enables a clean transfer of the image in the next stage avoiding the background charges from sparking to the heated blanket 145 and damaging the image and, in time, the photo imaging plate 135 and the heated blanket 145.

The cleaning station 175 is used to remove residual ink on the photo imaging plate 135 after the second transfer has taken place. In some examples, the cleaning station 175 also cools the photo imaging plate 135 from heat transferred during contact with the heated blanket 145. The photo imaging plate 135 is then ready to be recharged by the charging unit 110 ready for the next image.

In some examples, the plurality of positions at which surface voltages are measured comprises at least one of the first and second positions. In other words, the surface voltage is measured at the first and second positions, and correction voltages are applied to those positions. In other examples, the plurality of positions at which surface voltages are measured does not comprise at least one of the first and second positions. Correction voltages for the first and second voltages may then be determined by, for example, interpolating between voltages measured at other positions.

In some examples, the initiating application of the first correction voltage comprises at least one of the controller 117 controlling the charging unit 110 to apply the first correction voltage to the first position on the photoconductive layer 120, and the controller 117 controlling the charging unit 110 to apply the second correction voltage to the second position on the photoconductive layer 120.

In other examples, the apparatus 100 comprises an element other than the charging unit 110, wherein the element is controllable by the controller to apply at least one of the first correction voltage to the first position on the photoconductive layer and the second correction voltage to the second position on the photoconductive layer. For example, the element may comprise an intermediate unit as described above, such as an intermediate transfer drum.

In examples, the apparatus 100 comprises a photoconductive drum. The photoconductive drum may for example be the photoconductive unit 105. The photoconductive drum comprises the photoconductive layer. The photoconductive drum is controllable by the controller 117 to rotate during the measuring of surface voltages of the photoconductive layer. Measuring the surface voltages comprises measuring a dependence of surface voltage on a characteristic of the photoconductor drum. The characteristic may comprise duration of rotation, speed of rotation, angle of rotation and longitudinal position. In other examples, measuring the surface voltages comprises measuring a dependence of surface voltage on more than one of these characteristics. In one example, the controller 117 controls the photoconductive drum to rotate at a known angular velocity and controls the measuring unit 115 to measure surface voltage of the photoconductive layer 120 as a function of duration of rotation, which may be converted into rotation angle of the photoconductive drum. In another example, the controller 117 controls the measuring unit 115 to measure surface voltage of the photoconductive layer 120 as a direct function of angle of rotation of the photoconductive drum. In a further example, the controller 117 controls the measuring unit 115 to measure surface voltage of the photoconductive layer 120 as a function of longitudinal position along the photoconductive layer 120. In an example, the controller 117 controls the measuring unit to measure surface voltage of the photoconductive layer 120 as a two-dimensional function of angular position and longitudinal position, for example expressed as cylindrical polar coordinates.

Figure 2:
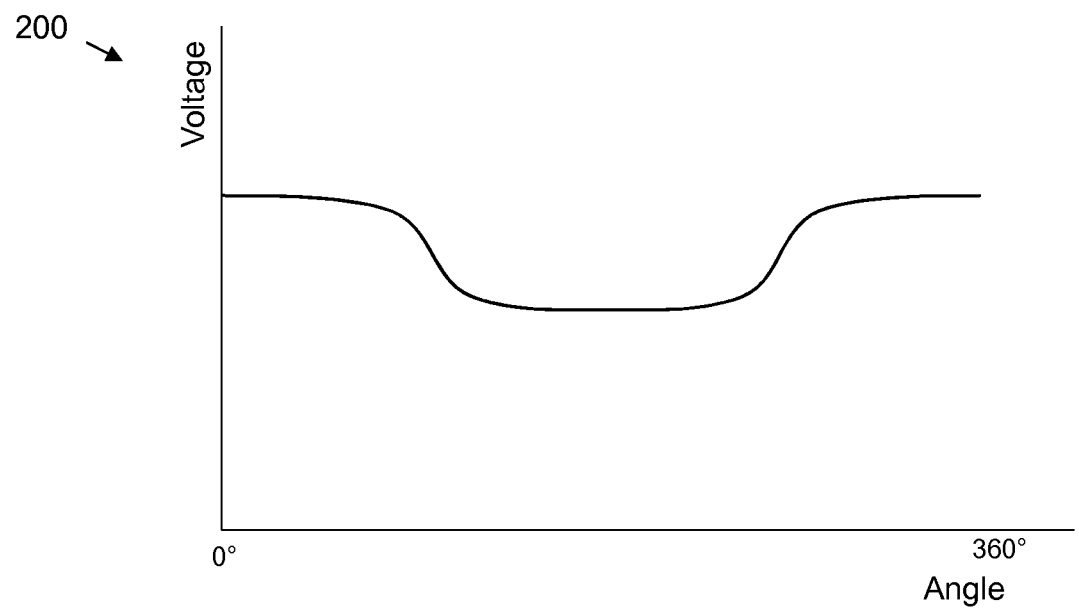
FIGS. 2 and 3 are schematic representations of photoconductor surface charge before and after applying correction voltages according to an example.
Figure 3:
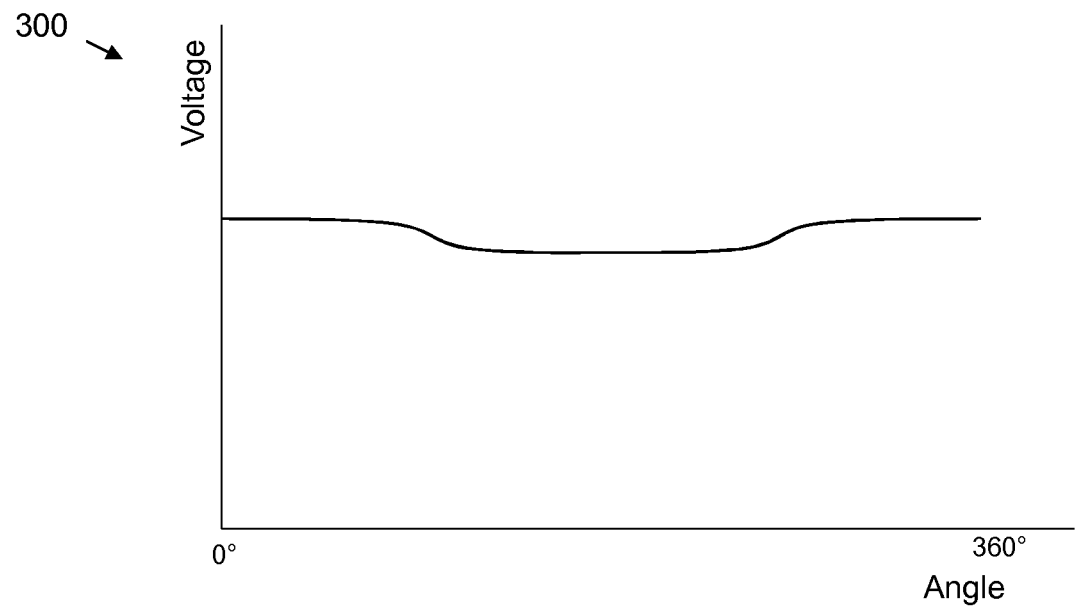

FIG. 2 shows a schematic representation 200 of measurements of surface charge of the photoconductive layer 120, following application of the charging voltage as a function of rotation angle according to examples. The non-uniformity of the surface charge is apparent. FIG. 3 shows a schematic representation 300 of surface charge of the photoconductive layer 120 following application of the correction voltages according to examples. The uniformity of surface charge has improved relative to that shown in FIG. 2.

Figure 4:
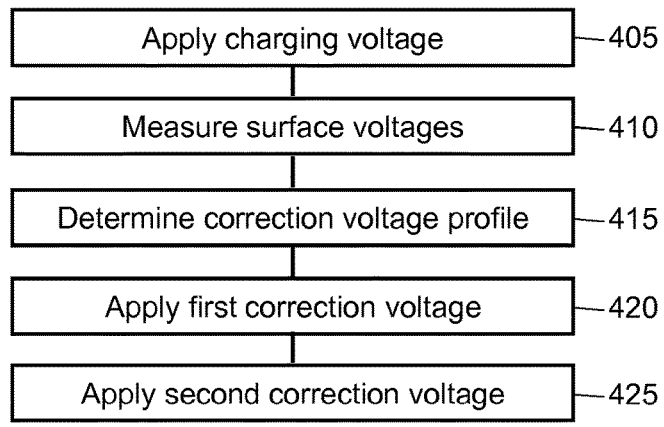
FIG. 4 is a flow diagram depicting a method for charging a photoconductive layer in an image forming apparatus according to an example.

FIG. 4 is a flow diagram depicting a method 400 for charging a photoconductive layer 120 in an image forming apparatus, according to an example.

At block 405, a charging voltage is applied to the photoconductive layer 120. At block 410, surface voltages of the photoconductive layer 120 are measured at a plurality of positions on the photoconductive layer 120.

At block 415, a correction voltage profile is determined based on the measured surface voltages. The determined correction voltage profile comprises at least a first correction voltage associated with a first position on the photoconductive layer 120, and a second correction voltage associated with a second position on the photoconductive layer 120. In an example, the plurality of positions comprises angular positions of the photoconductive layer 120, and/or the first position comprises an angular position of the photoconductive layer 120, and/or the second position comprises an angular position of the photoconductive layer 120.

At block 420 the first correction voltage is applied to the photoconductive layer 120. In some examples, the first correction voltage is applied to the first position on the photoconductive layer. In some examples, the first correction voltage is applied to a position other than the first position on the photoconductive layer.

At block 430 the second correction voltage is applied to the photoconductive layer 120. In some examples, the second correction voltage is applied to the second position on the photoconductive layer. In some examples, the second correction voltage is applied to a position other than the second position on the photoconductive layer.

In an example, determining the correction voltage comprises determining a polynomial fit based on the measured surface voltages. For example, the polynomial fit may comprise a least squares fit of the measured surface voltages to a polynomial of pre-defined order. The determined polynomial is then used to calculate the correction voltage profile.

In an example, determining the correction voltage profile comprises inputting the measured surface voltages to a look-up table, determining a first output of the look-up table corresponding to the first position and determining a second output of the look-up table corresponding to the second position. The look-up table thus allows a correction voltage to be determined based on an input measured surface voltage.

In an example, determining the correction voltage profile comprises determining a measured voltage profile based on the measured surface voltages. The correction voltage profile is then determined based on the measured voltage profile such that the correction voltage profile is an opposite charging profile to the measured voltage profile. In one such example, the measured voltage profile describes voltage as a function of angle of the photoconductive layer, for example as shown in FIG. 2. The opposite charging profile comprises an inversion of this, such that a lower voltage is applied at angles of the photoconductive layer 120 with higher measured surface voltage, and a higher voltage is applied at angles of the photoconductive layer 120 with lower measured surface voltage.

In an example, the correction voltage profile is determined such that application of the first and second correction voltages increases the uniformity of surface voltages of the photoconductive layer 120, for example as described above in relation to FIGS. 2 and 3.

Figure 5:
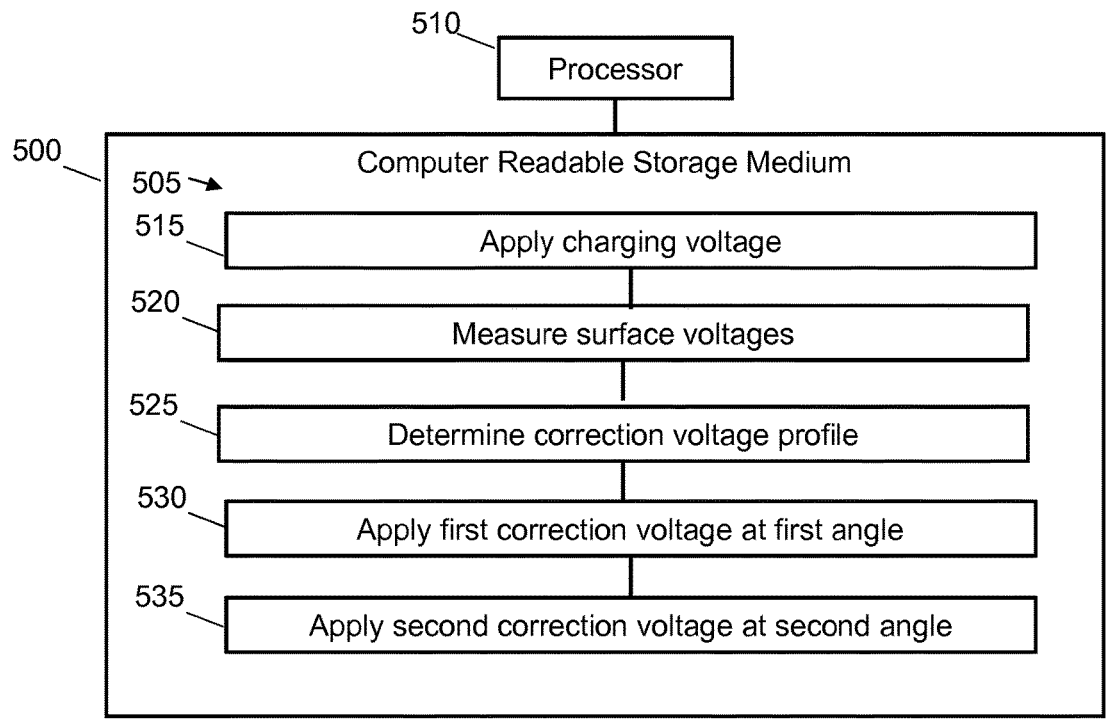
FIG. 5 is a schematic representation of a non-transitory computer-readable storage medium according to an example.

FIG. 5 shows a schematic representation of an example of a non-transitory computer-readable storage medium 500 comprising a set of computer readable instructions 505 which, when executed by at least one processor 510, cause the processor 510 to perform a method according to examples described herein. The computer readable instructions 505 may be retrieved from a machine-readable media, e.g. any media that can contain, store, or maintain programs and data for use by or in connection with an instruction execution system. In this case, machine-readable media can comprise any one of many physical media such as, for example, electronic, magnetic, optical, electromagnetic, or semiconductor media. More specific examples of suitable machine-readable media include, but are not limited to, a hard drive, a random access memory (RAM), a read-only memory (ROM), an erasable programmable read-only memory, or a portable disc.

In an example, instructions 505 cause the processor 510 to, at block 515, apply a charging voltage to a photoconductive layer 120.

At block 520, the instructions 505 cause the processor 510 to measure surface voltages of the photoconductive layer 120 at a plurality of rotation angles of the photoconductive layer 120.

At block 525, the instructions 505 cause the processor 510 to, based on the measured surface voltages, determine a correction voltage profile. The determined correction voltage profile comprises at least a first correction voltage associated with a first rotation angle of the photoconductive layer 120 and a second correction voltage associated with a second rotation angle, different to the first rotation angle, of the photoconductive layer 120.

At block 530, the instructions 505 cause the processor 510 to apply the first correction voltage to the photoconductive layer 120 at the first rotation angle.

At block 535, the instructions 505 cause the processor 510 to apply the second correction voltage to the photoconductive layer 120 at the second rotation angle.

The preceding description has been presented to illustrate and describe examples of the principles described. This description is not intended to be exhaustive or to limit these principles to any precise form disclosed. Many modifications and variations are possible in light of the above teaching. It is to be understood that any feature described in relation to any one example may be used alone, or in combination with other features described, and may also be used in combination with any features of any other of the examples, or any combination of any other of the examples.

What is claimed is:

1. An image forming apparatus comprising:
    a photoconductive unit comprising a photoconductive layer;
    a charging unit;
    a measuring unit; and
    a controller, wherein:
    the charging unit is controllable by the controller to apply a charging voltage to the photoconductive layer;
    the measuring unit is controllable by the controller to measure surface voltages of the photoconductive layer at a plurality of rotational positions on the photoconductive layer;
    the controller to:
    based on the measured surface voltages, determine a correction voltage profile, wherein the determined correction voltage profile comprises:
        a first correction voltage associated with a first rotational position on the photoconductive layer; and
        a second correction voltage associated with a second rotational position, different to the first rotational position, on the photoconductive layer;
    initiate application of the first correction voltage to the first rotational position on the photoconductive layer; and
    initiate application of the second correction voltage to the second rotational position on the photoconductive layer.

2. An image forming apparatus according to claim 1, wherein the plurality of rotational positions at which surface voltages are measured comprises at least one of the first and second rotational positions.

3. An image forming apparatus according to claim 1, wherein the initiating application of the first correction voltage comprises at least one of:
    the controller controlling the charging unit to apply the first correction voltage to the first rotational position on the photoconductive layer; and
    the controller controlling the charging unit to apply the second correction voltage to the second rotational position on the photoconductive layer.

4. An image forming apparatus according to claim 1, wherein the charging unit comprises a charge roller.

5. An image forming apparatus according to claim 1, further comprising:
    an element, other than the charging unit, controllable by the controller to apply at least one of the first correction voltage to the first rotational position on the photoconductive layer and the second correction voltage to the second rotational position on the photoconductive layer.

6. An image forming apparatus according to claim 5, wherein the element is an intermediate transfer drum.

7. An image forming apparatus according to claim 1, comprising a photoconductor drum, wherein:
    the photoconductor drum comprises the photoconductive layer;
    the photoconductor drum is controllable by the controller to rotate during the measuring of surface voltages of the photoconductive layer;
    measuring the surface voltages comprises measuring a dependence of surface voltage on a characteristic of the photoconductor drum.

8. An image forming apparatus according to claim 7, wherein the characteristic comprises at least one of duration of rotation, speed of rotation, angle of rotation and longitudinal position.

9. A method for charging a photoconductive layer in an image forming apparatus, the method comprising:
  applying a charging voltage to the photoconductive layer;
  measuring surface voltages of the photoconductive layer at a plurality of angular positions on the photoconductive layer;
  based on the measured surface voltages, determining a correction voltage profile, wherein the determined correction voltage profile comprises at least:
    a first correction voltage associated with a first angular position on the photoconductive layer; and
    a second correction voltage associated with a second angular position, different to the first angular position, on the photoconductive layer;
  applying the first correction voltage to the first angular position on the photoconductive layer; and
  applying the second correction voltage to the second angular position on the photoconductive layer.

10. A method according to claim 9, wherein determining the correction voltage profile comprises determining a polynomial fit based on the measured surface voltages.

11. A method according to claim 9, wherein determining the correction voltage profile comprises:
  inputting the measured surface voltages to a look-up table;
  determining a first output of the look-up table corresponding to the first angular position; and
  determining a second output of the look-up table corresponding to the second angular position.

12. A method according to claim 9, wherein determining the correction voltage profile comprises:
  based on the measured surface voltages, determining a measured voltage profile; and
  based on the measured voltage profile, determining the correction voltage profile such that the correction voltage profile is an opposite charging profile to the measured voltage profile.

13. A method according to claim 9, comprising determining the correction voltage profile such that application of the first and second correction voltages increases the uniformity of surface voltages of the photoconductive layer.

14. A method according to claim 9, wherein:
  the photoconductive layer comprises a photoconductive drum comprising the photoconductive layer;
  the photoconductive drum is to rotate during the measuring of surface voltages of the photoconductive layer;
  measuring the surface voltages comprises measuring a dependence of surface voltage on a characteristic of the photoconductive drum.

15. A method according to claim 14, wherein the characteristic comprises at least one of duration of rotation, speed of rotation, angle of rotation and longitudinal position.

16. A non-transitory computer-readable storage medium comprising a set of computer-readable instructions stored thereon which, when executed by at least one processor, cause the at least one processor to:
  apply a charging voltage to a photoconductive layer;
  measure surface voltages of the photoconductive layer at a plurality of rotation angles of the photoconductive layer;
  based on the measured surface voltages, determine a correction voltage profile, wherein the determined correction voltage profile comprises at least:
    a first correction voltage associated with a first rotation angle of the photoconductive layer; and
    a second correction voltage associated with a second rotation angle, different to the first rotation angle, of the photoconductive layer;
  applying the first correction voltage to the photoconductive layer at the first rotation angle; and
  applying the second correction voltage to the photoconductive layer at the second rotation angle.

17. A non-transitory computer-readable storage medium according to claim 16, wherein:
  the photoconductive layer comprises a photoconductive drum comprising the photoconductive layer;
  the photoconductive drum is to rotate during the measure of surface voltages of the photoconductive layer;
  the measure of surface voltages comprises measure of a dependence of surface voltage on a characteristic of the photoconductive drum.

18. A non-transitory computer-readable storage medium according to claim 17, wherein the characteristic comprises at least one of duration of rotation, speed of rotation, angle of rotation and longitudinal position.

* * * * *